United States Patent
Kim et al.

(10) Patent No.: US 11,486,964 B2
(45) Date of Patent: Nov. 1, 2022

(54) VEHICLE AND AUTOMATIC CONTROL METHOD FOR EMOTIONAL ENVIRONMENT THEREOF

(71) Applicants: Hyundai Motor Company, Seoul (KR); Kia Motors Corporation, Seoul (KR)

(72) Inventors: Gyun Ha Kim, Incheon (KR); Dae Yun An, Gyeonggi-do (KR); Eung Hwan Kim, Seoul (KR); Jeong Gi Yun, Seoul (KR); Seul Ki Jeon, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 471 days.

(21) Appl. No.: 16/672,687

(22) Filed: Nov. 4, 2019

(65) Prior Publication Data
US 2020/0400784 A1 Dec. 24, 2020

(30) Foreign Application Priority Data
Jun. 20, 2019 (KR) .................. 10-2019-0073452

(51) Int. Cl.
| | |
|---|---|
| *G01S 7/41* | (2006.01) |
| *B60Q 3/80* | (2017.01) |
| *B60Q 9/00* | (2006.01) |
| *B60H 1/00* | (2006.01) |
| *A61B 5/00* | (2006.01) |
| *A61B 5/113* | (2006.01) |
| *B60N 2/56* | (2006.01) |
| *A61B 5/08* | (2006.01) |
| *A61B 5/11* | (2006.01) |

(52) U.S. Cl.
CPC ............ *G01S 7/415* (2013.01); *A61B 5/4809* (2013.01); *A61B 5/6893* (2013.01); *A61B 5/742* (2013.01); *B60H 1/00742* (2013.01); *B60Q 3/80* (2017.02); *B60Q 9/00* (2013.01); *A61B 5/0816* (2013.01); *A61B 5/113* (2013.01); *A61B 5/1118* (2013.01); *B60N 2/56* (2013.01)

(58) Field of Classification Search
CPC ....................................................... G01S 7/415
See application file for complete search history.

(56) References Cited

U.S. PATENT DOCUMENTS

| | | | |
|---|---|---|---|
| 2007/0176402 A1* | 8/2007 | Irie ........................ | G06V 40/10 382/224 |
| 2017/0258398 A1* | 9/2017 | Jackson ............... | A61B 5/0507 |
| 2018/0065504 A1* | 3/2018 | Lan .................... | G08B 21/0263 |

(Continued)

OTHER PUBLICATIONS

G. Gutierrez et al., "Respiratory rate variability in sleeping adults without obstructive sleep apnea", Physiological Reports, 4(17), pp. 1-9 (2016).

*Primary Examiner* — Travis R Hunnings
(74) *Attorney, Agent, or Firm* — Fox Rothschild LLP

(57) ABSTRACT

A method for automatically controlling an emotional environment in a vehicle is provided. The method includes generating reflected wave information by radiating an electromagnetic wave toward a rear seat of the vehicle and receiving a reflected wave. A degree of activity is determined based on the reflected wave information and at least one device installed within the vehicle is operated based on the degree of activity.

18 Claims, 8 Drawing Sheets

(56) References Cited

U.S. PATENT DOCUMENTS

| | | | | |
|---|---|---|---|---|
| 2018/0167044 | A1* | 6/2018 | Kanagaraj | H04R 3/00 |
| 2020/0282803 | A1* | 9/2020 | Upmanue | B60N 2/879 |
| 2020/0285842 | A1* | 9/2020 | Wang | G06V 40/174 |
| 2020/0307483 | A1* | 10/2020 | Topf | G01S 7/412 |
| 2020/0391763 | A1* | 12/2020 | Yamamoto | B60W 50/16 |
| 2021/0039652 | A1* | 2/2021 | Ito | A61B 5/02055 |
| 2021/0114603 | A1* | 4/2021 | Dadam | F01N 9/00 |

* cited by examiner

| PEAK | 1 | 2 | 3 | 4 | 5 | 6 | ... | 18 | AVERAGE |
|---|---|---|---|---|---|---|---|---|---|
| PEAK-POINT TIME (SECOND) | 3 | 7 | 9.5 | 15 | 17 | 21 | ... | 55 | |
| PEAK-PEAK TIME DIFFERENCE (SECOND) | | 4 | 2.5 | 4.5 | 2 | 4 | ... | ... | |
| PEAK-PEAK TIME DIFFERENCE INCREASE /DECREASE RATE (%) (ABSOLUTE VALUE) | | | 37.5 | 80 | 55.5 | 100 | ... | ... | 68.3 |

FIG. 7

| DEGREE OF ACTIVITY | | STEP 0 (NO OCCUPANT) | STEP 1 (SLEEP STATE) | STEP 2 (INTERMEDIATE STATE) | STEP 3 (WAKE-UP STATE) |
|---|---|---|---|---|---|
| | | NO MOVEMENT/ NO RESPIRATION | NO MOVEMENT/ REGULAR RESPIRATION (RRV OF LESS THAN 44%) | NO MOVEMENT AND IRREGULAR RESPIRATION OR MOVEMENT AND REGULAR RESPIRATION | MOVEMENT/ IRREGULAR RESPIRATION (RRV OF 55% OR MORE) |
| LIGHT | BRIGH-TNESS | TURN OFF AMBIENT LIGHT IN REAR SEAT | SOFT LIGHTING | HIGHER BRIGHTNESS THAN THAT IN STEP 1 | HIGHER BRIGHTNESS THAN THAT IN STEP 2 |
| | COLOR | | PERSONALIZED COLOR 1 | PERSONALIZED COLOR 2 | CHANGE COLOR EVERY PREDETER-MINED TIME |
| SPEAKER | | TURN UP VOLUME OF SPEAKER IN REAR SEAT, CHANGE DIRECTIONAL ANGLE OF SOUND TOWARD DRIVER | ENTER SILENT MODE | TURN DOWN VOLUME OF SPEAKER IN REAR SEAT | ACTIVATE ALL SPEAKERS, SET DIRECTIONAL ANGLE OF SOUND TO BE DIRECTED TOWARD CENTER OF VEHICLE, SET INDEPENDENT SOUND FIELDS ex) SET SEPARATE SOUNDS FOR DRIVER'S SEAT AND REAR SEAT |
| TEMPERATURE CONTROL | | EXECUTE DRIVER ONLY MODE | → MAINTAIN TEMPERATURE / RAISE AIR CONDITIONING INTENSITY ← MAINTAIN TEMPERATURE / LOWER AIR CONDITIONING INTENSITY | | |
| SUNROOF | | - | CLOSED | - | - |
| DISPLAY DEVICE | | - | INFORM DRIVER THAT STATE OF OCCUPANT IS CHANGED TO SLEEP STATE, THROUGH CLUSTER, LCD, OR AVN | - | INFORM DRIVER THAT STATE OF OCCUPANT IS CHANGED TO WAKE-UP STATE, THROUGH CLUSTER, LCD, OR AVN |

FIG. 8

VEHICLE AND AUTOMATIC CONTROL METHOD FOR EMOTIONAL ENVIRONMENT THEREOF

CROSS-REFERENCE TO RELATED APPLICATION

This application claims the benefit of priority to Korean Patent Application No. 10-2019-0073452, filed on Jun. 20, 2019, the entire contents of which are incorporated herein by reference.

TECHNICAL FIELD

The present disclosure relates to a vehicle for automatically controlling an emotional environment in the vehicle and an automatic control method for an emotional environment thereof.

BACKGROUND

In general, when a person is seated on a rear seat within a vehicle, a driver of the vehicle has to directly check a state (e.g., a sleep state or a wake-up state) of the occupant on the rear seat or discern the state of the occupant through conversation, and directly determine states of a light, a speaker, an air conditioner, and the like that are appropriate for the state of the person, and directly operate control devices thereof.

Accordingly, these various factors contribute to the attention distraction of the driver, thus increasing an accident risk In particular, when the occupant on the rear seat is an infant incapable of speech, the light, the speaker, the air conditioner, and the like may be required to be operated more carefully. However, the driver may not be able to check a state of the infant through conversation, and the driver may be unable to directly check the state of the infant depending on the form of a car seat.

SUMMARY

The present disclosure provides a vehicle for automatically controlling an emotional environment depending on a result obtained by monitoring a state of an occupant on a rear seat of the vehicle, and an automatic control method for an emotional environment thereof.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, a method for automatically controlling an emotional environment in a vehicle may include generating reflected wave information by radiating an electromagnetic wave toward a rear seat of the vehicle and receiving a reflected wave, determining a degree of activity based on the reflected wave information, and operating at least one device installed within the vehicle based on the degree of activity.

According to another aspect of the present disclosure, a vehicle may include a radar sensor configured to generate reflected wave information by radiating an electromagnetic wave toward a rear seat of the vehicle and receive a reflected wave, and a controller configured to determine a degree of activity based on the reflected wave information and operate at least one device installed within the vehicle based on the degree of activity.

According to another aspect of the present disclosure, a vehicle may include a radar sensor configured to generate reflected wave information by radiating an electromagnetic wave toward a rear seat of the vehicle and receive a reflected wave, a controller configured to determine a degree of activity based on the reflected wave information, and at least one device configured to perform a predetermined operation based on the degree of activity.

BRIEF DESCRIPTION OF THE DRAWINGS

The above and other objects, features and advantages of the present disclosure will be more apparent from the following detailed description taken in conjunction with the accompanying drawings:

FIGS. 6 and 7 are views illustrating a method for discerning a respiration pattern of an occupant on a rear seat according to an exemplary embodiment of the present disclosure; and FIG. 8 is a table illustrating step S40 of FIG. 3 according to an exemplary embodiment of the present disclosure.

DETAILED DESCRIPTION

Figure 1:
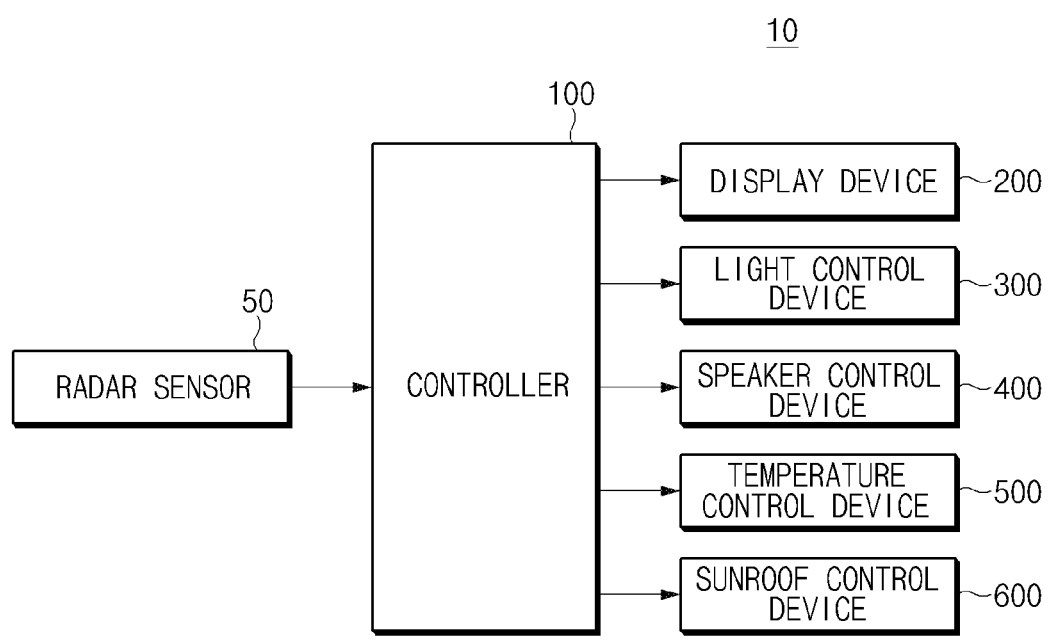
FIG. 1 is a schematic view illustrating a vehicle according to an exemplary embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/of" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the exemplary embodiment of the present disclosure, a detailed description of well-known features or functions will be ruled out in order not to unnecessarily obscure the gist of the present disclosure.

In describing the components of the exemplary embodiment according to the present disclosure, terms such as first, second, "A", "B", (a), (b), and the like may be used. These terms are merely intended to distinguish one component from another component, and the terms do not limit the nature, sequence or order of the components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

Figure 2:
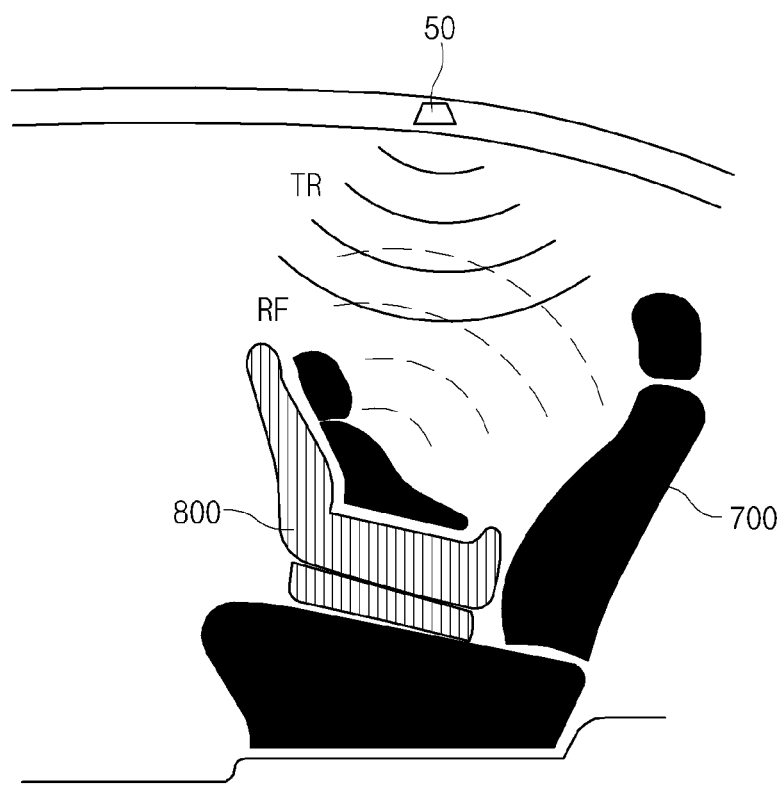
FIG. 2 is a view illustrating an operating method of a radar sensor of FIG. 1 according to an exemplary embodiment of the present disclosure.

FIG. 1 is a schematic view illustrating a configuration of a system according to an exemplary embodiment of the present disclosure. FIG. 2 is a view illustrating an operating method of a radar sensor of FIG. 1. Referring to FIG. 1, the configuration of the system that is applicable to a transportation type, including a vehicle, is schematically illustrated. Hereinafter, for convenience of description, it may be assumed that the system is a vehicle. The vehicle 10 has a function of monitoring a state of a person seated on a rear seat of the vehicle 10, informing a driver of the state of the person on the rear seat, and automatically providing an emotional environment appropriate for the state of the person. The emotional environment refers to an environment that the occupant uses the five senses to feel. The emotional environment may be created by a light, a speaker, temperature control, a sunroof, and the like. For example, the emotional environment may include a desired temperature, a desired volume, a sunshade, etc.

The vehicle 10 may include a radar sensor 50, a controller 100, a display device 200, a light control device 300, a speaker control device 400, a temperature control device 500, and a sunroof control device 600. The controller 100 may be configured to operate the various components of the vehicle 10. In particular, the radar sensor 50 may be configured to monitor a state of a person seated or located on a rear seat of the vehicle 10. The radar sensor 50 may be configured to radiate electromagnetic waves having a specific wavelength (e.g., ultra-high frequency waves having a wavelength in the range of about 10 cm to 100 cm) toward the rear seat of the vehicle 10, receive reflected waves reflected from an object located on the rear seat, and generate reflected wave information for discerning a presence or absence of a person, a movement of the person, a respiration pattern of the person, and the like.

Referring to FIG. 2, the radar sensor 50 may be installed in a roof panel disposed above a rear seat 700. The radar sensor 50 may be configured to radiate electromagnetic waves (TR) having a specific wavelength toward the rear seat 700, receive reflected waves (RF) reflected from an object located on the rear seat 700, and generate reflected wave information. The reflected wave information may include a change in reflected wave intensity over time. The reflected wave intensity may represent the distance from the object, and the unit thereof may be decibel (dB). However, the scope of the present disclosure is not limited thereto.

When a baby or infant is sitting in a car seat 800 attached to the rear seat 700 as illustrated in FIG. 2, or when a person is directly sitting on the rear seat 700, the radar sensor 50 may be configured to radiate electromagnetic waves TR toward the baby or the person, receive reflected waves RF reflected from the baby or the person, and generate reflected wave information. Referring again to FIG. 1, the radar sensor 50 may be configured to transfer the reflected wave information to the controller 100.

The controller 100 may be configured to detect and distinguish a movement, respiration, and a respiration pattern of the occupant on the rear seat, based on the reflected wave information received from the radar sensor 50 and may be configured to determine a degree of activity based on the movement, the respiration, and the respiration pattern of the person. In addition, the controller 100 may be configured to store, in advance, a control table in which operations of the devices 200 to 600 that correspond to degrees of activity are listed, and may be configured to extract operations of the devices 200 to 600 that correspond to the currently determined degree of activity, with reference to the control table. The controller 100 may be configured to operate the devices 200 to 600.

The display device 200 may be configured to provide visual information to the driver. The display device 200 may be at least one of, for example, a cluster and an audio, video, and navigation (AVN). The light control device 300 may be configured to adjust on/off, brightness, and color of each lamp installed within the vehicle 10. In particular, the light control device 300 may be configured to adjust on/off, brightness, and color of an ambient light installed in a rear seat. The color may include a plurality of colors, and a specific color, among the plurality of colors, may be set to a personalized color (e.g., personalized color 1 or personalized color 2) by a user in advance.

The speaker control device 400 may be configured to adjust on/off, volume, and sound field of each speaker installed within the vehicle 10. A plurality of speakers may be installed at various positions (e.g., a dashboard, a front door, a rear door, a rear surface of a rear seat, and the like) within the vehicle 10, and the speaker control device 400 may be configured to adjust the volumes of the plurality of speakers to change a directional angle of sound. For example, the speaker control device 400 may be configured to adjust the volumes of the plurality of speakers to be the same to set the directional angle of sound to be directed toward the center of the vehicle 10 and may be configured to increase the volumes of speakers located on a rear seat to be greater than the volumes of speakers located on a front seat to set the directional angle of sound to be directed toward the driver.

The temperature control device 500 may be configured to adjust on/off, temperatures, and intensities of an air conditioner installed within the vehicle 10 and a heating seat and a cooling seat of a front or rear seat. The sunroof control device 600 may be configured to adjust opening/closing of a sunroof installed in the vehicle 10. According to an exemplary embodiment, the sunroof may be operated together with or independently of a sunshade. The components 50 to 600 of the vehicle 10 illustrated in FIG. 1 may transmit and receive data therebetween via controller area network (CAN) communication for in-vehicle communication. The CAN communication may be configured to classify the plurality of components 50 to 600 into a plurality of categories. The plurality of components 50 to 600 may belong to the same category or different categories.

Figure 3:
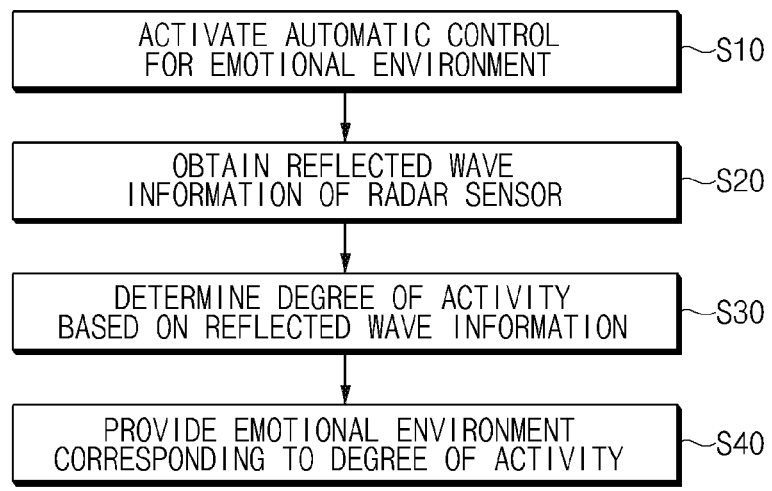
FIG. 3 is a flowchart illustrating an automatic control method for an emotional environment according to an exemplary embodiment of the present disclosure.

FIG. 3 is a flowchart illustrating an automatic control method for an emotional environment according to an exemplary embodiment of the present disclosure. Referring to FIG. 3, a user may activate or deactivate an automatic control option for an emotional environment through an audio video navigation (AVN) or a separate button. The automatic control option for the emotional environment refers to a function of monitoring a state of a person on a rear seat, informing a driver of the state of the person, and automatically providing an emotional environment appropriate for the state of the person.

When the automatic control option for the emotional environment is activated by the user (S10), the radar sensor 50 may be configured to radiate electromagnetic waves having a specific wavelength (e.g., ultra-high frequency waves having a wavelength in the range of about 10 cm to 100 cm), receive reflected waves, and generate reflected wave information for discerning a presence or absence of a person, a movement of the person, a respiration pattern of the person, and the like, and the controller 100 may be configured to obtain the reflected wave information from the radar sensor 50 (S20).

The controller 100 may be configured to detect and distinguish a movement, respiration, and a respiration pattern of the occupant located on the rear seat, based on the reflected wave information and may be configured to determine a degree of activity based on the movement, the respiration, and the respiration pattern of the person (S30). In addition, the controller 100 may be configured to determine the degree of activity every predetermined period (e.g., one minute). The controller 100 may be configured to store, in advance, a control table in which operations of the devices 200 to 600 that correspond to degrees of activity are listed, and may be configured to extract operations of the devices 200 to 600 that correspond to the currently determined degree of activity, with reference to the control table. The degree of activity represents the activity of the person located on the rear seat, and in the control table, operations of the devices 200 to 600 for creating a more dynamic emotional environment match a higher degree of activity, and operations of the devices 200 to 600 for creating a more static emotional environment match a lower degree of activity.

Further, the controller 100 may be configured to operate the devices 200 to 600 to provide an emotional environment corresponding to each degree of activity. The automatic control method for the emotional environment according to the exemplary embodiment of the present disclosure may automatically provide an emotional environment based on a state of a person located on a rear seat without intervention of a driver, thereby ensuring safety driving and improving satisfaction of the occupant on the rear seat.

Figure 4:
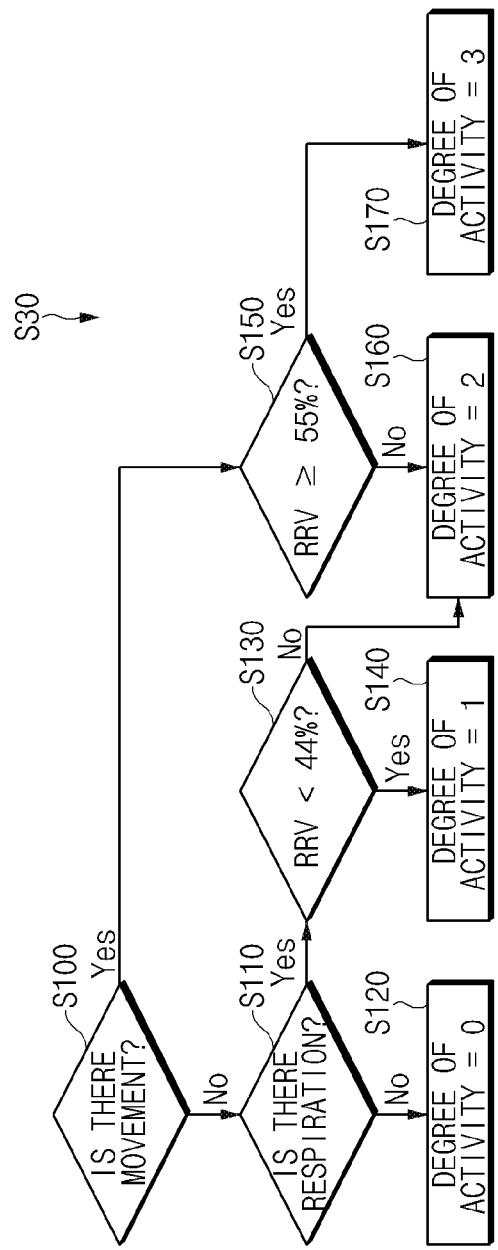
FIG. 4 is a detailed flowchart illustrating step S30 illustrated in FIG. 3 according to an exemplary embodiment of the present disclosure.
Figure 5:
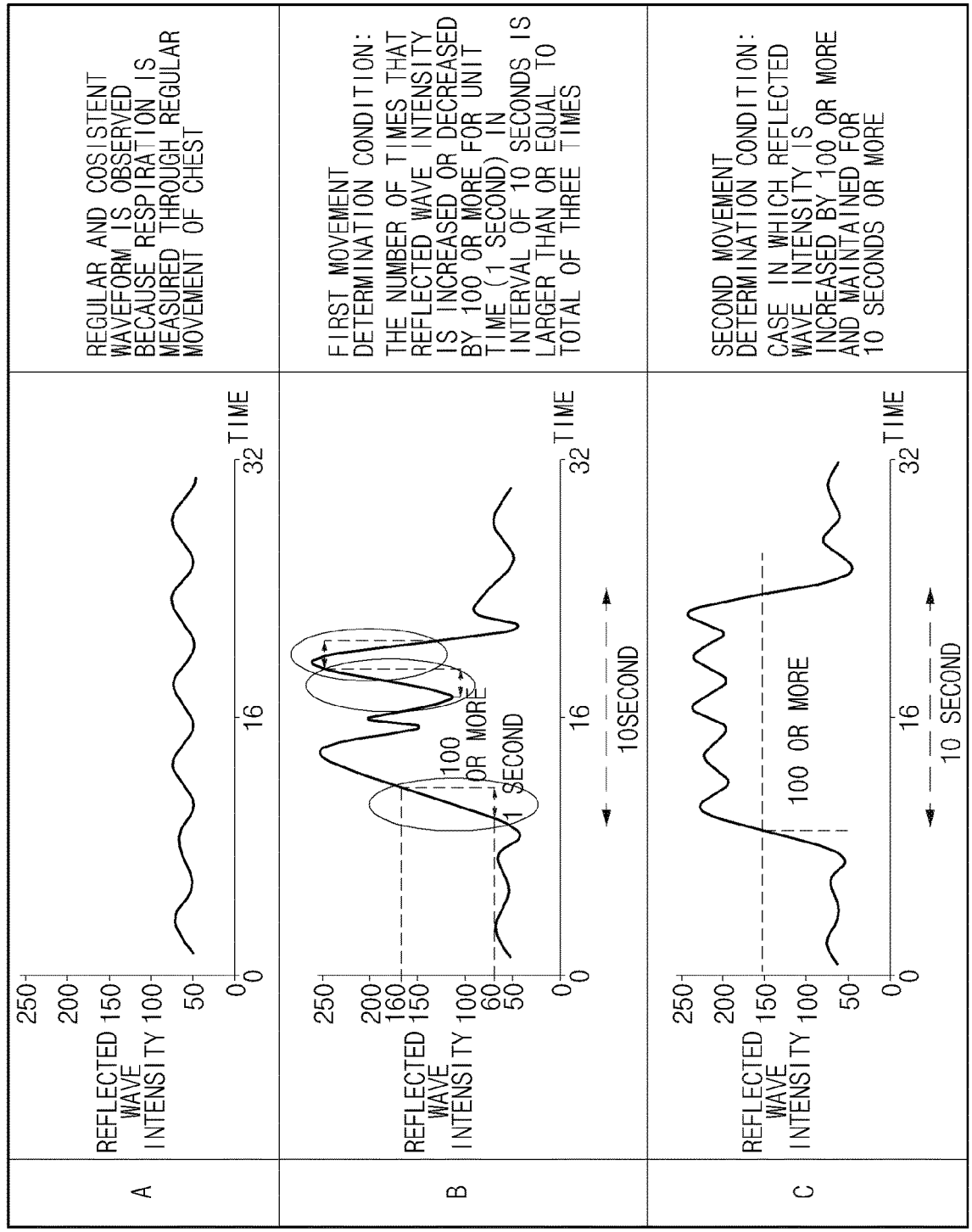
FIG. 5 is a view illustrating a method for determining whether an occupant on a rear seat moves according to an exemplary embodiment of the present disclosure.
Figure 6:
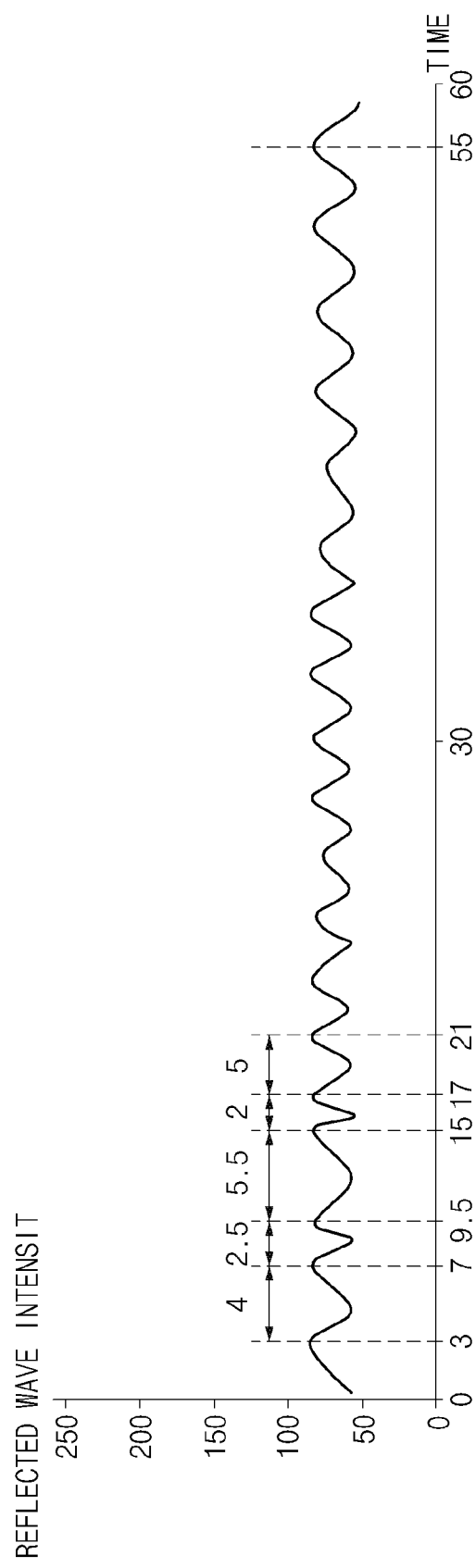

FIG. 4 is a detailed flowchart illustrating step S30 illustrated in FIG. 3. FIG. 5 is a view illustrating a method for determining whether an occupant on a rear seat moves. FIGS. 6 and 7 are views illustrating a method for discerning a respiration pattern of an occupant on a rear seat. Referring to FIG. 4, the controller 100 may be configured to determine whether there is a movement of an occupant on a rear seat, based on reflected wave information (S100). Referring to FIG. 5, cases A, B, and C are illustrated. Case A represents a case where there is no movement of an occupant on a rear seat, and cases B and C represent cases where there is a movement of an occupant on a rear seat.

First, case A represents a case where only respiration is observed without a movement of an occupant on a rear seat. Since respiration may be measured through a regular movement of the chest of a person, the waveform of reflected wave intensity over time may be observed in a regular and consistent waveform (e.g., a waveform similar to a sinusoidal wave). When the waveform of the reflected wave intensity does not satisfy any one of movement conditions that will be described in cases B and C, the controller 100 may be configured to determine that in the current interval, there is no movement of an occupant on a rear seat.

Next, case B represents a case where there is a movement of an occupant on a rear seat. The movement of the person refers to that the occupant on the rear seat moves the body, and due to the movement of the person, the waveform of reflected wave intensity over time is irregular, and a drastic change in the reflected wave intensity may be observed. The controller 100 may be configured to determine whether the waveform of the reflected wave intensity satisfies a first movement condition. The first movement condition may be a condition in which the number of times that the reflected wave intensity is increased or decreased by a specific magnitude or more (e.g., about 100 or more) for unit time (e.g., about one second) in an interval of predetermined time (e.g., about 10 seconds) is greater than or equal to a specific number of times (e.g., about three times).

Furthermore, the controller 100 may be configured to determine whether the waveform of the reflected wave intensity satisfies a second movement condition. The second movement condition may be a condition in which the reflected wave intensity is increased by the specific magnitude or more (e.g., about 100 or more) and maintained for the predetermined time (e.g., about 10 seconds) or more. When the waveform of the reflected wave intensity satisfies at least one of the first movement condition and the second movement condition, the controller 100 may be configured to determine that there is a movement of an occupant on a rear seat. In contrast, when the waveform of the reflected wave intensity does not satisfy any one of the first movement condition and the second movement condition, the controller 100 may be configured to determine that there is no movement of an occupant on a rear seat.

Referring again to FIG. 4, in response to determining that there is no movement of an occupant on a rear seat (No in S100), the controller 100 may be configured to determine whether there is respiration of an occupant on a rear seat, based on the reflected wave information (S110). In particular, the controller 100 may be configured to extract peaks and troughs of the waveform of the reflected wave intensity for predetermined time (e.g., about 1 minute). The peaks refer to the reflected wave intensities at the time when the slope of the reflected wave intensity over time is changed from positive to negative, and the troughs refer to the reflected wave intensities at the time when the slope of the reflected wave intensity over time is changed from negative to positive.

The controller 100 may be configured to determine whether the average of the troughs for the predetermined time is greater than or equal to a threshold value (e.g., about 20), and when the average of the troughs is greater than or equal to the threshold value, the controller 100 may be configured to determine whether there is respiration, based on whether the reflected wave intensity has a predetermined pattern (e.g., a pattern similar to a sinusoidal wave that periodically increases and decreases within a predetermined range). In other words, when the average of the troughs is less than the threshold value or the reflected wave intensity does not have the predetermined pattern, the controller 100 may be configured to determine that there is no respiration of an occupant on a rear seat (there is no occupant). In contrast, when the average of the troughs is greater than or equal to the threshold value or the reflected wave intensity has the predetermined pattern, the controller 100 may be configured to determine that there is respiration of an occupant on a rear seat (e.g., an occupant is detected).

When there is no respiration of an occupant on a rear seat (No in S110), the controller 110 may be configured to determine the degree of activity to be "0" (S120). When the degree of activity is "0", the controller 110 may be configured to determine there is no occupant on a rear seat. When respiration of an occupant on a rear seat is detected (Yes in S110), the controller 100 may be configured to calculate respiration rate variability (RRV) based on the reflected wave information. In particular, the RRV refers to a change in time difference between respiration and respiration, and a sleep step such as wake-up, rapid eye movement (REM) sleep, deep sleep, or the like may be determined based on the RRV. The sleep state is closer to deep sleep as the RRV decreases, and there is a greater possibility of wake-up as the RRV increases.

Referring to FIGS. 6 and 7, an exemplary embodiment of calculating RRV is illustrated. The controller 100 may be configured to extract peaks of the waveform of reflected wave intensity for predetermined time (e.g., 1 minute) and calculate time differences between the continuous peaks. In the exemplary embodiment illustrated in FIG. 6, peaks occur at 3 seconds, 7 seconds, 9.5 seconds, 15 seconds, 17 seconds, 21 seconds, . . . 55 seconds, and the time differences between the peaks (peak-peak time differences) correspond to 4 seconds, 2.5 seconds, 5.5 seconds, 2 seconds, 5 seconds, . . . .

Changes in the time differences between the peaks (peak-peak time difference increase/decrease rates) that are calculated from the time differences between the peaks are −37.5%, +80%, −55.5%, +100%, . . . . The controller 100 may be configured to obtain 68.3 by calculating the average of absolute values of the changes in the time differences between the peaks, and determine RRV to be 68.3.

The RRV calculation method described in FIGS. 6 and 7 is merely an exemplary embodiment of the present disclosure, and it may be possible to calculate RRV by another method (e.g., by calculating the average of absolute values of the changes in the time differences between troughs). Referring again to FIG. 4, when the RRV is less than 44% (Yes in S130), the controller 100 may be configured to determine the degree of activity to be "1" (S140). When the degree of activity is "1", that the controller 110 may be configured to determine that the occupant on the rear seat is in a sleep state.

When the RRV is 44% or greater (No in S130), the controller 100 may be configured to determine the degree of activity to be "2" (S160). When the degree of activity is "2", the controller 110 may be configured to determine that the occupant on the rear seat is in an intermediate state between a sleep state and a wake-up state. In response to determining that there is a movement of the occupant on the rear seat (Yes in S100), the controller 100 may be configured to determine the degree of activity based on the RRV (S150). When the RRV is less than 55% (No in S150), the controller 100 may be configured to determine the degree of activity to be "2" (S160). In other words, when the degree of activity is "2", that the controller 110 may be configured to determine that a respiration pattern is irregular even though there is no movement, or a respiration pattern is relatively regular although there is a movement. When the RRV is 55% or greater (Yes in S150), the controller 100 may be configured to determine the degree of activity to be "3" (S170). When the degree of activity is "3", the controller 110 may be configured to determine that there is a movement and a respiration pattern is irregular (that is, a state in which the person is awake).

The detailed conditions (e.g., time, the number of times, the threshold value, and the like) for determining the movement, the respiration, and the RRV of the occupant on the rear seat as described above are merely illustrative, and the scope of the present disclosure is not limited thereto. The detailed conditions may be varied depending on the characteristics of the vehicle structure and the characteristics of the main occupant, and a menu through which the user directly sets the sensitivity may be provided through the AVN to prevent a malfunction of the automatic control for the emotional environment.

Although only the method of determining the movement, the respiration, and the RRV of the occupant on the rear seat using the reflected wave information of the radar sensor 50 has been described above, the scope of the present disclosure is not limited thereto. In other words, the respiration and the RRV may be determined using at least one of the radar sensor 50, a camera, a $CO_2$ sensor, a respiration measuring instrument, and an infrared sensor, and the movement may be determined using at least one of the radar sensor 50, an ultrasonic sensor, a camera, and a pressure sensor.

FIG. 8 is a table illustrating step S40 of FIG. 3. Referring to FIG. 8, to provide an emotional environment corresponding to each of the degrees of activity, the controller 100 may be configured to operate the devices 200 to 600 to correspond to the degree of activity.

First, when the degree of activity corresponds to step "0", the controller 100 may be configured to determine that is no movement and respiration of an occupant on a rear seat. Further, this refers to a state in which there is no occupant. The controller 100 may be configured to extract, from a control table, operations of the devices 200 to 600 that correspond to the degree of activity of step "0" and may be configured to operate the devices 200 to 600. The light control device 300 may be configured to turn off an ambient light installed in the rear seat.

Further, the speaker control device 400 may be configured to turn up or increase the volume of a speaker disposed around the rear seat and change the directional angle of sound toward the driver. The aim is to provide a high-resolution sound service to the driver since there is no occupant on the rear seat. The temperature control device 500 may be configured to turn off a heating seat and a cooling seat of the rear seat and operate in a driver only mode to operate an air conditioner installed in a front seat according to control of the driver. The aim is to minimize unnecessary power waste.

When the degree of activity corresponds to step "1", the controller 100 may be configured to determine that is no movement of an occupant on the rear seat and respiration is regular (RRV of less than 44%). Further, this refers to a state in which the occupant is in a sleep state. The controller 100 may be configured to extract, from the control table, operations of the devices 200 to 600 that correspond to the degree of activity of step "1" and operate the devices 200 to 600.

The light control device 300 may be configured to set the brightness of the ambient light installed in the rear seat to soft lighting and set the color of the ambient light to personalized color 1. In particular, the brightness of the soft lighting and the personalized color 1 may be default values, or may be values determined by the user in advance. The speaker control device 400 may be configured to enter all speakers installed within the vehicle 10 in a silent mode to change all the speakers into a mute state.

The temperature control device 500 may be configured to maintain the temperatures of the air conditioner and the heating and cooling seats of the rear seat and decrease the intensities of the air conditioner and the heating and cooling seats of the rear seat. The intensities of the air conditioner and the heating and cooling seats of the rear seat may be increased as the degree of activity increases from step 1 to step 3. The sunroof control device 600 may be configured to close a sunroof or maintain the sunroof in a closed state.

Additionally, the display device 200 may be configured to display a notification that the state of the occupant on the rear seat is changed to the sleep state, to the driver through at least one of a cluster and an AVN. When the degree of activity is changed to step "1", that is, when the state of the occupant on the rear seat is changed to the sleep state, the priority of operation may be determined in the order of the speaker control device 400, the light control device 300, the sunroof control device 600, and the temperature control device 500. The aim is to immediately generate an emotional environment that does not disturb the sleep of the occupant on the rear seat.

According to an exemplary embodiment, the priority may be identically or similarly applied even in the case of a change to a different degree of activity. When the degree of activity corresponds to step "2", the controller 100 may be configured to determine that there is no movement of an occupant on the rear seat and respiration is irregular (RRV of 44% or more) or there is a movement and respiration is regular (RRV of less than 55%). Further, this refers to a state in which the occupant is in an intermediate state between a sleep state and a wake-up state. The controller 100 may be configured to extract, from the control table, operations of the devices 200 to 600 that correspond to the degree of activity of step "2" and operate the devices 200 to 600.

The light control device 300 may be configured to set the brightness of the ambient light installed in the rear seat to be higher than soft lighting and set the color of the ambient light to personalized color 2. In particular, the brightness of the light and the personalized color 2 may be default values, or may be values determined by the user in advance. The speaker control device 400 may be configured to relatively turn down or decrease the volume of the speaker installed in the rear seat. In particular, the volume may be lowered to a preset percentage (e.g., about 50% of the current volume), or may be lowered to a preset value (e.g., step 3 among a total of 10 steps).

Additionally, the temperature control device 500 may be configured to maintain the temperatures of the air conditioner and the heating and cooling seats of the rear seat and increase the intensities of the air conditioner and the heating and cooling seats of the rear seat to be greater than those when the degree of activity corresponds to step "1". When the degree of activity corresponds to step "3", the controller 100 may be configured to determine that there is a movement of an occupant on the rear seat and respiration is irregular (RRV of 55% or more). Further, this refers to a state in which the occupant is in a wake-up state. The controller 100 may be configured to extract, from the control table, operations of the devices 200 to 600 that correspond to the degree of activity of step "3" and may control the devices 200 to 600.

The light control device 300 may be configured to set the brightness of the ambient light installed in the rear seat to be higher than that when the degree of activity corresponds to step "2" and set the color of the ambient light to be changed every predetermined time (e.g., about 10 seconds). In particular, the brightness of the light, the sequence and types of changed colors, and holding time for each color may be default values, or may be values determined by the user in advance.

The speaker control device 400 may be configured to activate all of the speakers installed within the vehicle 10. The speaker control device 400 may be configured to set the directional angle of sound to be directed toward the center of the vehicle 10 or set the sound field of the speaker installed in the front seat and the sound field of the speaker installed in the rear seat to be independent of each other. For example, the sound field of the speaker installed in the front seat may be set to a sound filed in which bass is not emphasized, and the sound field of the speaker installed in the rear seat may be set to a sound field in which bass is emphasized.

The temperature control device 500 may be configured to maintain the temperatures of the air conditioner and the heating and cooling seats of the rear seat and increase the intensities of the air conditioner and the heating and cooling seats of the rear seat to be greater than those when the degree of activity corresponds to step "2". The display device 200 may be configured to display a notification that the state of the occupant on the rear seat is changed to the wake-up state, to the driver through at least one of the cluster and the AVN.

The total number of steps of the degree of activity and the control methods of the devices 200 to 600 for each step, which are illustrated in FIG. 8, are illustrative. The scope of the present disclosure is not limited thereto.

The operations of the method or the algorithm described in connection with the exemplary embodiments disclosed herein may be embodied directly in hardware or a software module executed by a processor, or in a combination thereof. The software module may reside on a storage medium (that is, a memory and/or storage) such as a RAM, a flash memory, a ROM, an EPROM, an EEPROM, a register, a hard disk, a removable disk, or a CD-ROM. The exemplary storage medium may be coupled to the processor, and the processor may read information out of the storage medium and may record information in the storage medium. Alternatively, the storage medium may be integrated with the processor. The processor and the storage medium may reside in an application specific integrated circuit (ASIC). The ASIC may reside within a user terminal. In another case, the processor and the storage medium may reside in the user terminal as separate components.

According to the exemplary embodiments of the present disclosure, the vehicle and the automatic control method for the emotional environment thereof may automatically provide an emotional environment depending on a state of a person located on a rear seat without intervention of a driver, thereby ensuring safety driving and improving satisfaction of the occupant on the rear seat.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the exemplary embodiments of the present disclosure are provided to explain the spirit and scope of the present disclosure, but not to limit them, so that the spirit and scope of the present disclosure is not limited by the exemplary embodiments. The scope of the present disclosure should be construed on the basis of the accompanying claims, and all the technical ideas within the scope equivalent to the claims should be included in the scope of the present disclosure.

What is claimed is:

1. A method for automatically controlling an emotional environment in a vehicle, comprising:
   generating, by a controller, reflected wave information by radiating an electromagnetic wave toward a rear seat of the vehicle and receiving a reflected wave;
   determining, by the controller, a degree of activity based on the reflected wave information; and
   operating, by the controller, at least one device installed in the vehicle based on the degree of activity;
   wherein the determining of the degree of activity includes:
      determining, by the controller, a movement of an occupant on the rear seat, based on the reflected wave information; and
      determining, by the controller, the degree of activity based on the movement of the occupant on the rear seat;
      wherein the movement of the occupant on the rear seat is determined based on whether a waveform of reflected wave intensity satisfies at least one of a plurality of movement conditions; and
      wherein the plurality of movement conditions include a condition in which the number of times that the reflected wave intensity is increased or decreased by a specific magnitude or more for unit time in an interval of predetermined time is greater than or equal to a specific number of times and a condition in which the reflected wave intensity is increased by the specific magnitude or more and maintained for the predetermined time or more.

2. The method of claim 1, wherein a radar sensor configured to radiate the electromagnetic wave is installed in a roof panel disposed above the rear seat.

3. The method of claim 1, wherein the reflected wave information includes a change in reflected wave intensity over time.

4. The method of claim 1, wherein the determining of the degree of activity includes:
   determining, by the controller, respiration, and a respiration pattern of an occupant on the rear seat, based on the reflected wave information; and
   determining, by the controller, the degree of activity based on the respiration and the respiration pattern of the occupant on the rear seat.

5. The method of claim 4, wherein the respiration of the occupant on the rear seat is determined based on whether reflected wave intensity has a predetermined pattern.

6. The method of claim 4, wherein the respiration pattern of the occupant on the rear seat is obtained by calculating the average of absolute values of changes in time differences between continuous peaks of a waveform of reflected wave intensity extracted for predetermined time.

7. The method of claim 1, wherein the operating of the at least one device installed in the vehicle includes:
   determining, by the controller, the operation of the at least one device that corresponds to the degree of activity, with reference to a control table in which the degree of activity and the operation of the at least one device match each other.

8. The method of claim 1, wherein when the degree of activity represents that there is no occupant on the rear seat, the operating of the at least one device installed in the vehicle includes:
   turning off, by the controller, an ambient light installed in the rear seat;
   turning up, by the controller, a volume of a speaker located around the rear seat and changing a directional angle of sound toward a driver; and
   turning off, by the controller, a heating seat and a cooling seat of the rear seat and operating an air conditioner installed in a front seat according to control of the driver.

9. The method of claim 1, wherein when the degree of activity represents that an occupant on the rear seat is in a sleep state, the operating of the at least one device installed in the vehicle includes:
   setting, by the controller, brightness of an ambient light installed in the rear seat to a reduced lighting and setting color of the ambient light to a first personalized color;
   switching, by the controller, all speakers of the vehicle to a mute state;
   maintaining, by the controller, temperatures of an air conditioner and heating and cooling seats of the rear seat and lowering intensities of the air conditioner, the heating seat, and the cooling seat; and
   closing, by the controller, a sunroof or maintaining the sunroof in a closed state.

10. The method of claim 9, wherein the operating of the at least one device installed in the vehicle further includes:
    displaying, by the controller, a notification that a state of the occupant on the rear seat is changed to the sleep state, to a driver through at least one of a cluster and an audio video navigation (AVN).

11. The method of claim 1, wherein when the degree of activity represents that an occupant on the rear seat is in an intermediate step between a sleep state and a wake-up state, the operating of the at least one device installed in the vehicle includes:
- setting, by the controller, brightness of an ambient light installed in the rear seat to be higher than a reduced lighting and setting color of the ambient light to a second personalized color;
- turning down, by the controller, a volume of a speaker located in the rear seat; and
- maintaining, by the controller, temperatures of an air conditioner and heating and cooling seats of the rear seat and increasing intensities of the air conditioner, the heating seat, and the cooling seat to be greater than those when the degree of activity represents that the occupant on the rear seat is in the sleep state.

12. The method of claim 1, wherein when the degree of activity represents that an occupant on the rear seat is in a wake-up state, the operating of the at least one device installed in the vehicle includes:
- setting, by the controller, brightness of an ambient light installed in the rear seat to be higher than that when the degree of activity represents that the occupant on the rear seat is in an intermediate state between a sleep state and the wake-up state, and setting color of the ambient light to be changed every predetermined time;
- activating, by the controller, all speakers installed within the vehicle and setting a directional angle of sound to be directed toward the center of the vehicle; and
- maintaining, by the controller, temperatures of an air conditioner and heating and cooling seats of the rear seat and increasing intensities of the air conditioner, the heating seat, and the cooling seat to be greater than those when the degree of activity represents that the occupant on the rear seat is in the intermediate step between the sleep state and the wake-up state.

13. The method of claim 12, wherein the operating of the at least one device installed in the vehicle further includes:
- displaying, by the controller, a notification that a state of the occupant on the rear seat is changed to the wake-up state, to a driver through at least one of a cluster and an audio video navigation (AVN).

14. A vehicle, comprising:
- a radar sensor configured to generate reflected wave information by radiating an electromagnetic wave toward a rear seat of the vehicle and receiving a reflected wave; and
- a controller configured to:
  - determine a degree of activity based on the reflected wave information; and
  - operate at least one device installed within the vehicle based on the degree of activity;
- wherein the determining of the degree of activity includes:
  - determining, by the controller, a movement of an occupant on the rear seat, based on the reflected wave information; and
  - determining, by the controller, the degree of activity based on the movement of the occupant on the rear seat;
- wherein the movement of the occupant on the rear seat is determined based on whether a waveform of reflected wave intensity satisfies at least one of a plurality of movement conditions; and
- wherein the plurality of movement conditions include a condition in which the number of times that the reflected wave intensity is increased or decreased by a specific magnitude or more for unit time in an interval of predetermined time is greater than or equal to a specific number of times and a condition in which the reflected wave intensity is increased by the specific magnitude or more and maintained for the predetermined time or more.

15. The vehicle of claim 14, wherein the radar sensor is installed in a roof panel disposed above the rear seat.

16. The vehicle of claim 14, wherein the controller is configured to:
- determine and a respiration pattern of an occupant on the rear seat, based on the reflected wave information; and
- determine the degree of activity based on the respiration, and the respiration pattern of the occupant on the rear seat.

17. The vehicle of claim 14, wherein the controller is configured to determine the operation of the at least one device that corresponds to the degree of activity, with reference to a control table in which the degree of activity and the operation of the at least one device match each other.

18. A vehicle, comprising:
- a radar sensor configured to generate reflected wave information by radiating an electromagnetic wave toward a rear seat of the vehicle and receiving a reflected wave;
- a controller configured to determine a degree of activity based on the reflected wave information; and
- at least one device configured to perform a predetermined operation based on the degree of activity,
- wherein the determining of the degree of activity includes:
  - determining, by the controller, a movement of an occupant on the rear seat, based on the reflected wave information; and
  - determining, by the controller, the degree of activity based on the movement of the occupant on the rear seat;
- wherein the movement of the occupant on the rear seat is determined based on whether a waveform of reflected wave intensity satisfies at least one of plurality of movement conditions; and
- wherein the plurality of movement conditions include a condition in which the number of times that the reflected wave intensity is increased or decreased by a specific magnitude or more for unit time in an interval of predetermined time is greater than or equal to a specific number of times and a condition in which the reflected wave intensity is increased by the specific magnitude or more and maintained for the predetermined time or more.

* * * * *